United States Patent
Ross

(10) Patent No.: US 11,576,311 B2
(45) Date of Patent: *Feb. 14, 2023

(54) MONOKARYON MYCELIAL MATERIAL AND RELATED METHOD OF PRODUCTION

(71) Applicant: MycoWorks, Inc., Emeryville, CA (US)

(72) Inventor: Philip Ross, San Francisco, CA (US)

(73) Assignee: MycoWorks, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/699,328

(22) Filed: Mar. 21, 2022

(65) Prior Publication Data

US 2022/0210986 A1    Jul. 7, 2022

Related U.S. Application Data

(62) Division of application No. 16/663,269, filed on Oct. 24, 2019, now Pat. No. 11,277,981.

(Continued)

(51) Int. Cl.
*A01G 18/10* (2018.01)
*A01G 18/20* (2018.01)
(Continued)

(52) U.S. Cl.
CPC .............. *A01G 18/69* (2018.02); *A01G 18/10* (2018.02); *A01G 18/20* (2018.02); *A01G 18/60* (2018.02); *A01G 18/62* (2018.02)

(58) Field of Classification Search
CPC ........ A01G 18/10; A01G 18/20; A01G 18/22; A01G 18/60; A01G 18/61
(Continued)

(56) References Cited

U.S. PATENT DOCUMENTS 1,808,383 A * 6/1931 Steves ................ A01G 18/69
47/1.1
2,994,160 A * 8/1961 Sinden ................ A01G 18/60
47/1.1

(Continued)

FOREIGN PATENT DOCUMENTS

| CN | 104115674 A | 10/2014 |
| GB | 1566625 A | 5/1980 |
| WO | 9852403 A1 | 11/1998 |

OTHER PUBLICATIONS

Stamets, Paul et al., "The Mushroom Cultivator: A Practical Guide to Growing Mushrooms at Home", Jan. 1, 1983 (Jan. 1, 1983), pp. 15-126, XP055709474, available at https://library.uniteddiversity.coop/Permaculture/Mushroom_Cultivator-A_Practical_Guide_to_Growing_Mushrooms_at_Home.pdf, last accessed Oct. 31, 2022.

*Primary Examiner* — David J Parsley
(74) *Attorney, Agent, or Firm* — Temmerman Law; Mathew J. Temmerman

(57) ABSTRACT

A monokaryotic mycelium sheet producing system for creating a sheet of monokaryotic mycelial material. The mycelium sheet producing system includes a culture unit, a spore stock unit, a plating unit, a section unit, a sub-plating unit, an expanding unit and a colonization unit. The culture unit prepares a monokaryon culture. The spore stock unit grows a plurality of fruit bodies in sterile laboratory conditions to create a spore stock. The plating unit performs a peroxide-based spore rescue and a plating process. The section unit is adaptable to section robust hyphae. The sub-plating unit sub-plates and expands the robust hyphae onto a spawn grain master. The expanding unit subsequently expands the spawn grain master into appropriate production of spawn volume. The colonization unit is adaptable to perform a subsequent colonization of mycelium substrate thereby creating a substantially defect free sheet of mycelium.

14 Claims, 5 Drawing Sheets

Related U.S. Application Data

(60) Provisional application No. 62/749,717, filed on Oct. 24, 2018.

(51) Int. Cl.
    *A01G 18/69*     (2018.01)
    *A01G 18/62*     (2018.01)
    *A01G 18/60*     (2018.01)

(58) Field of Classification Search
    USPC .......................................................... 47/1.1
    See application file for complete search history.

(56) References Cited

U.S. PATENT DOCUMENTS

| | | | | |
|---|---|---|---|---|
| 3,118,249 | A * | 1/1964 | Bard et al. | A01G 18/62 47/65.9 |
| 3,292,305 | A * | 12/1966 | Stengel | A01G 18/62 47/1.1 |
| 4,159,225 | A | 6/1979 | Yoshikumi et al. | |
| 4,242,832 | A | 1/1981 | Eger et al. | |
| 4,337,594 | A * | 7/1982 | Hanacek | A01G 18/62 264/45.3 |
| 6,018,906 | A * | 2/2000 | Pia | A01G 18/62 47/1.1 |
| 6,378,244 | B1 * | 4/2002 | Iwata | A01G 18/20 47/1.1 |
| 7,971,388 | B2 * | 7/2011 | Kawai | A01G 18/20 47/1.1 |
| 9,485,917 | B2 * | 11/2016 | Bayer | A01G 18/50 |
| 11,032,982 | B2 * | 6/2021 | Ross | A01G 18/20 |
| 11,277,981 | B2 * | 3/2022 | Ross | A01G 18/60 |

* cited by examiner

MONOKARYON MYCELIAL MATERIAL AND RELATED METHOD OF PRODUCTION

RELATED APPLICATIONS

This application is a divisional application based on U.S. patent application Ser. No. 16/663,269 filed Oct. 24, 2019 and granted as U.S. Pat. No. 11,277,981 on Mar. 22, 2022, and which claims the benefit of U.S. provisional patent application 62/749,717, filed Oct. 24, 2018, the disclosures of which is incorporated herein in its entirety.

BACKGROUND OF THE DISCLOSURE

Technical Field of the Disclosure

The present embodiment relates generally to monokaryon strain development, and more particularly, to sheets of mycelium utilizing monokaryotic mycelial matter and methods of producing the same.

Description of the Related Art

In the fungus life cycle, a fungal spore germinates into a homokaryotic mycelium. Although the term "homokaryotic" in general refers to multinucleate cells where the nuclei are generally identical, in practice with respect to fungal spore germinates, these multinucleate cells are not strictly similar with each other. As is well understood, homokaryotic mycelia may join and reproduce sexually, yielding increases in genetic variability in the mycelial mass.

A single basidiospore germinates to give rise to a mass of monokaryotic hyphal filaments wherein each cell of which contains a single haploid nucleus. The complex interwoven mat of branching hyphae arising from a single spore is called the mycelium. Part of the mycelium grows submerged within the medium on which the fungus is growing, but aerial hyphae exist and produce abundant uninucleate haploid spores (oidia) which can germinate to complete an asexual cycle. The mycelium continues to grow as a monokaryon until it encounters a hypha from another fungus. At this point, hyphae from the two separate fungi fuse and determination of whether the mates are sexually compatible occurs intracellularly. If the two fungi are compatible, reciprocal nuclear migration occurs after cell fusion.

The morphology of the dikaryon differs from that of the monokaryon in several respects, but most distinctively, cells of the dikaryon undergo a complex form of cell division involving the formation of clamp connections to preserve one copy of each haploid nucleus within every dikaryotic cell. In contrast, the monokaryotic cell does not go through the normal reproductive process and thus does not generate fruiting bodies at any stage.

It is now understood that fungal tissue growth may be directed and controlled such that the resultant mycelial tissue has utility in various industries. In some cases, a sheet of mycelium biotextile is a result of these industrial processes, which upon harvest, can be cured and finished to take on qualities that are similar in texture, look and performance to plastics, foams and animal skins. A common use for these materials includes industries in which leather would conventionally be used. In these industries, the uniformity of the leather-like material is often of value. Fungi are very sensitive to stimuli in their environment and have the ability to alter the direction and vigor of growth of expanding hyphae in response to gravitropic, thermotropic, thigmotropic, phototropic, (chemotropic) and hydrotropic stimuli. It is understood that these growth factors may be manipulated in order to reduce the variability in the finished product.

Therefore, there is a need for an efficient and reliable system and method for creating large volumes of monokaryotic materials utilizing fewer resources and with a low environmental impact. Such a monokaryotic mycelial material producing system would refine a mycelial tissue product without amounts of post processing and would reduce genetic variability, blemishes and fruiting bodies. Such a system would produce the mycelial material with a high degree of uniformity in thickness and appearance and with a high degree of consistency from batch to batch. Moreover, such a system would produce the mycelium material utilizing minimum time, cost and complexity associated with minimizing variability and blemishes. The present embodiment accomplishes these objectives.

SUMMARY OF THE INVENTION

To minimize the limitations found in the prior art, and to minimize other limitations that will be apparent upon the reading of the specification, the present disclosure provides a monokaryotic mycelium sheet which is free or substantially free of defects. Preferably, the monokaryon cultures lack half their genetic material and also lack sex cell signal pathways that drive developmental behaviors of fruit formation. Therefore, the defects present in the resultant mycelial material are substantially reduced. In the preferred embodiment, a monokaryon strain of G. lingzhi and other fungi are used in the production of mycelium leather that does not express tissues associated with fruit body formation. However, any suitable fungi capable of monokaryotic growth may be utilized. In still other embodiments hybrid monokaryon strains may be created.

The disclosure also provides a mycelium sheet producing system comprising a culture unit for preparing a monokaryon culture utilizing a live culture sample of a fungal material. The system further includes a spore stock unit, a plating unit, a section unit, a sub-plating unit, an expanding unit and a colonization unit. In the preferred embodiment, the spore stock unit is designed to grow a plurality of fruit bodies in sterile laboratory conditions to create a spore stock. The plating unit performs a peroxide-based spore rescue and plating process. The section unit is adaptable to section robust hyphae. Preferably, the sub-plating unit sub-plates and expands the robust hyphae onto a spawn grain master. The expanding unit subsequently expands the spawn grain master into appropriate production of spawn volume. The colonization unit is adaptable to perform a subsequent colonization of substrate thereby creating the sheets of mycelium.

The preferred embodiment further provides a method for producing the monokaryotic mycelium sheet. The method is initiated by providing the mycelium sheet producing system. Next, the monokaryon culture is prepared at the culture unit utilizing the live culture sample of fungus. Then, the plurality of fruit bodies is grown in sterile conditions to create the spore stock at the spore stock unit. Thereafter, the peroxide-based spore rescue and plating process are performed at the plating unit. Upon successful germination of the peroxide-based spore, the robust hyphae are sectioned at the section unit. Next, the robust hyphae are sub-plated and expanded onto a spawn grain master at the sub-plating unit. Then, the spawn grain master is subsequently expanded into the appropriate production of spawn volume at the expanding unit. Finally, the subsequent colonization of substrate is performed thereby creating the sheet of mycelium at the colonization unit.

A first objective of the present invention is to provide a monokaryotic mycelial sheet producing system and method for creating large volumes of substantially or completely pure monokaryotic materials.

A second objective of the present invention is to provide a monokaryotic mycelial sheet producing system that refines a mycelial tissue product without heavy post processing and which produces a sheet with reduced genetic variability, blemishes and fruiting bodies as compared to any sheet found in nature.

A third objective of the present invention is to provide a monokaryotic mycelial sheet producing system for harvesting the mycelial material with a high degree of uniformity in thickness and appearance and also with a high degree of consistency from batch to batch.

A fourth objective of the present invention is to provide a monokaryotic mycelial sheet producing system that produces the mycelium material utilizing minimum time, cost and complexity associated with minimizing variabilities and blemishes.

These and other advantages and features of the present invention are described with specificity so as to make the present invention understandable to one of ordinary skill in the art.

BRIEF DESCRIPTION OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention, thus the drawings are generalized in form in the interest of clarity and conciseness.

DETAILED DESCRIPTION OF THE DRAWINGS

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized, and changes may be made without departing from the scope of the present invention.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below.

As used herein, the singular forms "a", "an" and "the" include plural referents unless the context clearly dictates otherwise. "And" as used herein is interchangeably used with "or" unless expressly stated otherwise. As used herein, the term "about" means +/−5% of the recited parameter. All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "wherein", "whereas", "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

Figure 1:
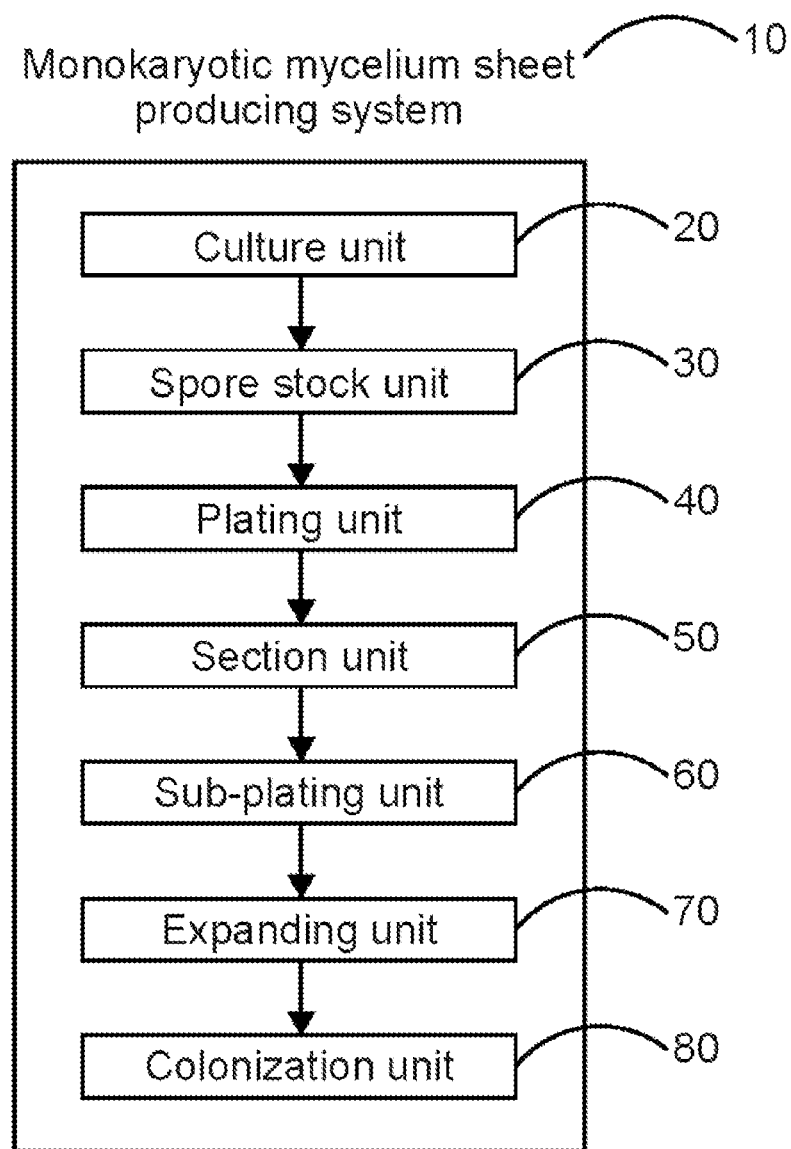
FIG. 1 is a schematic representation of a monokaryotic mycelium sheet producing system in accordance with the preferred embodiment of the present invention.

Referring to FIG. 1, a monokaryotic mycelium sheet producing system 10 for creating a sheet of monokaryotic mycelial material is illustrated. The mycelium sheet producing system 10 includes a culture unit 20 for preparing a monokaryon culture utilizing a live culture sample of a fungal material. The monokaryon culture is adaptable to prepare substantially defect free sheet or mass of mycelium. In the preferred embodiment, a monokaryon strain of G. lingzhi and other fungi are used in the production of mycelium leather that does not express tissues associated with fruit body formation. However, any suitable fungi capable of monokaryotic growth may be utilized. In still other embodiments, hybrid monokaryon strains may be created.

The mycelium sheet producing system 10 further includes a spore stock unit 30, a plating unit 40, a section unit 50, a sub-plating unit 60, an expanding unit 70 and a colonization unit 80. The spore stock unit 30 is designed to grow a plurality of fruit bodies in sterile laboratory conditions to create a spore stock. The plating unit 40 performs a peroxide-based spore rescue and plating process. The section unit 50 is adaptable to section robust hyphae. The sub-plating unit 60 sub-plates and expands the robust hyphae onto a spawn grain master. The expanding unit 70 subsequently expands the spawn grain master into an appropriate production of spawn volume. In one embodiment, the spawn volume is about 20 liters, however in other embodiment the volume may be greater or less than 20 liters. The colonization unit 80 is adaptable to perform a subsequent colonization of mycelium substrate thereby creating the sheet or mass of mycelium that is substantially or completely free of defects.

Figure 2:
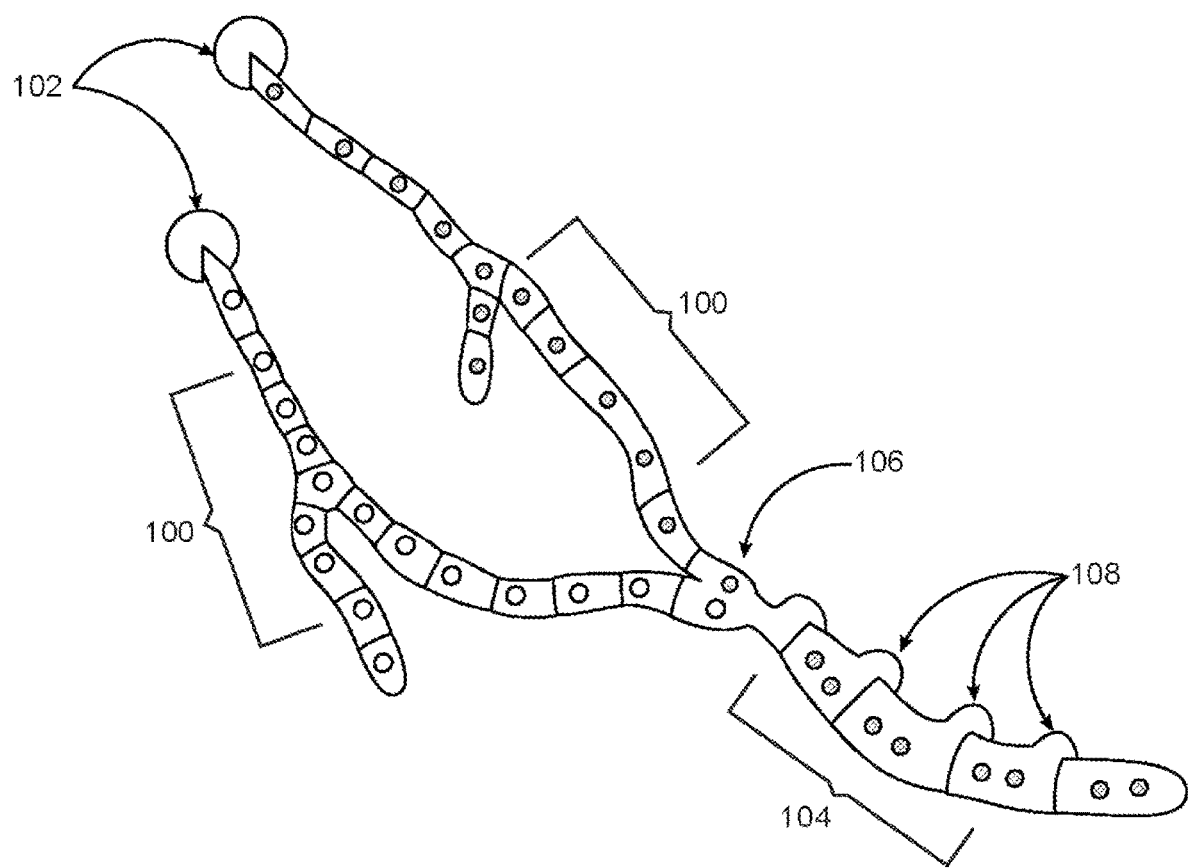
FIG. 2 is a diagrammatic image illustrating two monokaryons growing from two germinating spores in accordance with the preferred embodiment of the present invention.

FIG. 2 is a diagrammatic image illustrating two monokaryons 100 growing from two germinating spores 102. The mycelium sheet producing system 10 does not allow a dikaryon stage 104 and a plasmogamy stage 106 having the clamp connections 108. In the preferred embodiment, the fungal monokaryon cultures lack clamp connections 108 associated with Ganoderma tissue which might confer particular material qualities and mechanical properties to finished mycelium-based materials. Additionally, the expression of the cells and their constituent biochemistry is varied from that found in nature, which can alter the curing and finishing processes. Further, the monokaryon cultures lack half their genetic material and also lack sex cell signal pathways that drive developmental behaviors of fruit formation. Due to this, the defects present in the resultant mycelial material are substantially reduced. In the preferred embodiment, less than 10% of the surface of the mycelium material exhibits the formation of fruiting bodies and the cells of the mycelium material are monokaryotic. In other embodiments, less than 5% of the surface exhibits the formation of fruiting bodies, and in still other embodiments less than 1% of the surface exhibits the formation of fruiting bodies. Of note, the organism is not being genetically modified during this process.

In one embodiment the monokaryotic mycelium sheet producing system provides a growing space comprising a tray having a conveying platform and a permeable membrane with a plurality of pores positioned on the conveying platform; a substrate inoculated with a fungal strain positioned on the permeable membrane; a porous material positioned on top of the substrate; and a mass of mycelium grown within said growing space, the mass having a surface of which less than 10% of said surface exhibits the formation of fruiting bodies. In this or other embodiments, the system may be optimized such that the substrate weight to tray empty space volume ratio is between 0.5 and 5.0 g/cc, the tray empty space volume to substrate volume is between 0.01 and 1.0, the tray empty space volume to substrate area is between 0.5 and 5.0 cc/cm$^2$, wherein the $CO_2$ concentration is held above 3% in steady state conditions, the relative humidity is held above 40% in steady state conditions, and wherein the $O_2$ concentration is held below 20% in steady state conditions to promote mycelium growth without the fruiting body.

Figure 3:
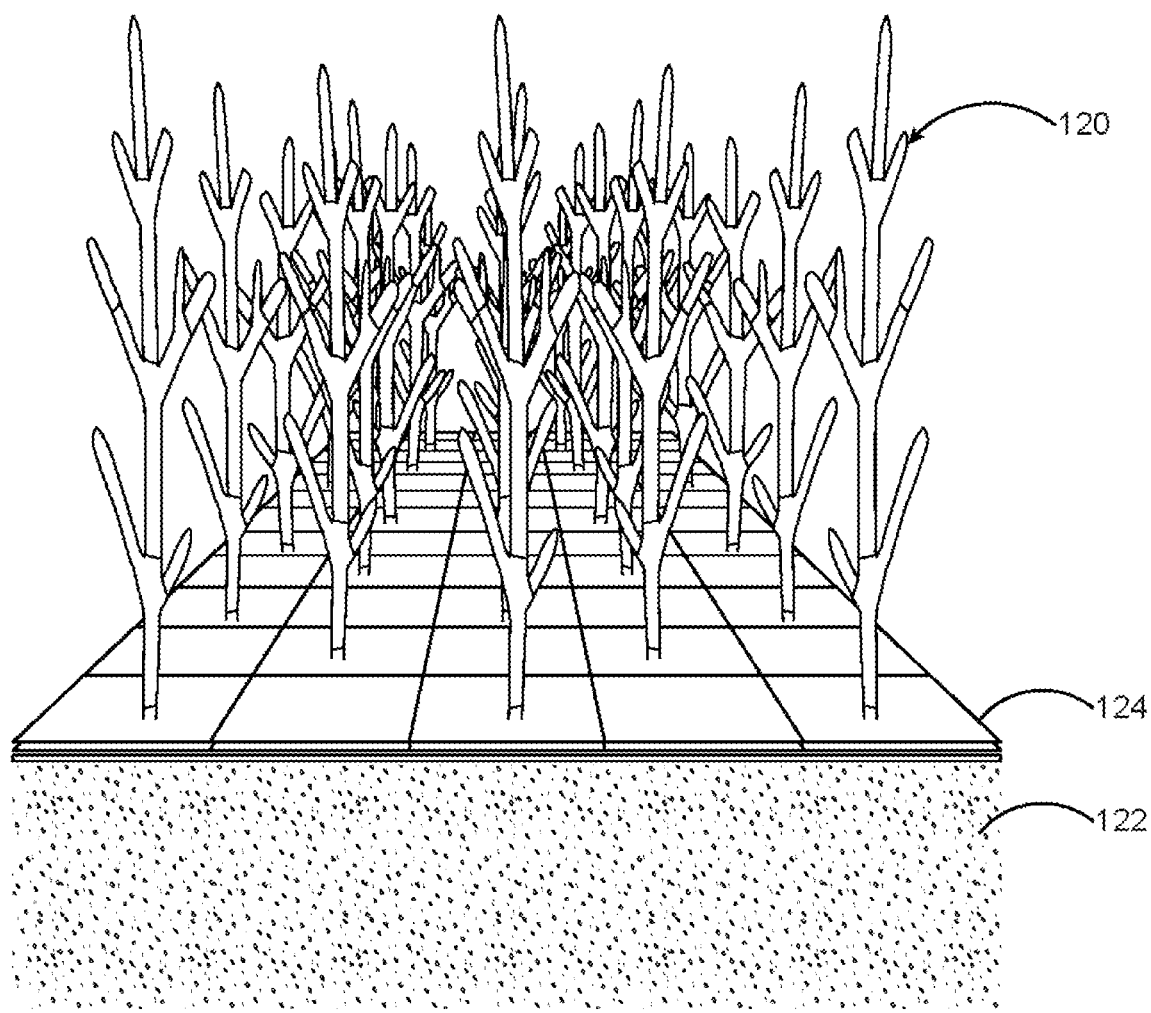
FIG. 3 is a perspective view of a monokaryotic hyphae growing in a mycelium growth bed in accordance with the preferred embodiment of the present invention.
Figure 4:
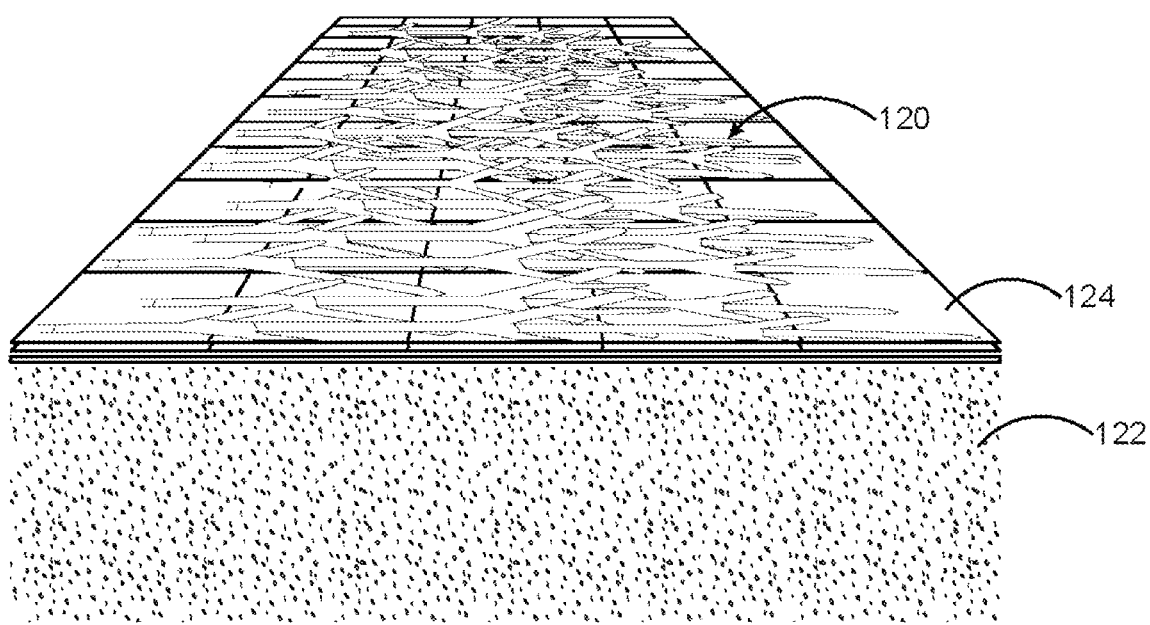
FIG. 4 is a perspective view of the monokaryotic hyphae flattened after grown in the mycelium growth bed in accordance with the preferred embodiment of the present invention.

Since mycelium-based leather-like materials are now of great interest in many markets, improved methods of harvesting such materials with a high degree of uniformity in thickness and appearance and a high degree of consistency from batch to batch have been required. Hence, it is highly recommended to grow and harvest the monokaryotic hyphae 120 in a mycelium growth bed 124 as shown in FIGS. 3 and 4. FIG. 3 shows the monokaryotic hyphae 120 grown from a mycelium substrate 122 in the mycelium growth bed 124. The mycelium growth bed 124 uniformly separates the hyphae 120 from the mycelium substrate 122 thereby providing a uniform expression of the mycelium material. The sheet of mycelium, upon harvest in the mycelium growth bed 124, can be cured and finished to take on qualities that are similar in texture, look and performance to plastics, foams and animal skins. The mycelium material may be physically manipulated into different patterns. FIG. 4 shows the monokaryotic hyphae 120 in a flattened stage for manipulation purpose. With the consistent and patterned manipulations, the fungal material can be formed in layered structures with determined arrangements of fungal tissue. Due to such physical manipulation of the fungal material, the hyphae can be grown into particular and determined directions such that they can be arranged into orthogonal structures, lattices, and other two-dimensional and three-dimensional organizations.

Figure 5:
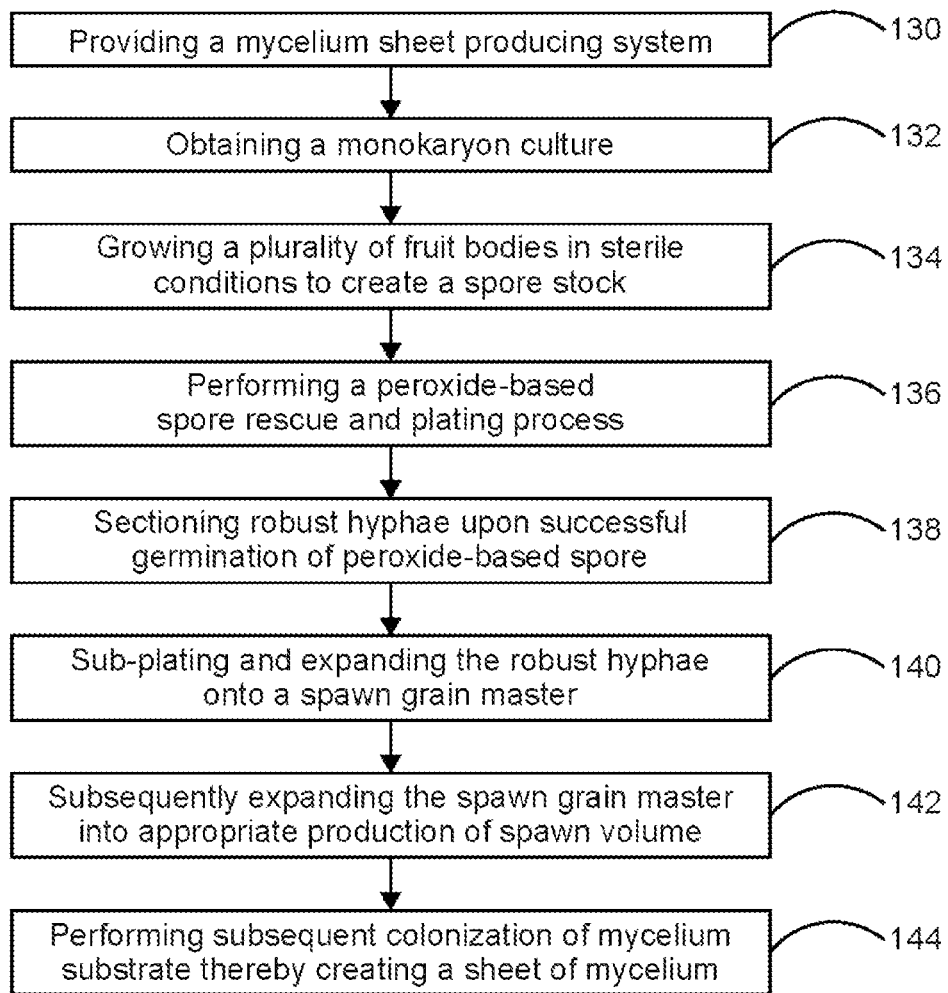
FIG. 5 is a flowchart of a method for producing the monokaryotic mycelium sheet in accordance with the preferred embodiment of the present invention.

FIG. 5 is a flowchart of a method for producing the monokaryotic mycelium sheet. The method commences by providing the mycelium sheet producing system as shown in block 130. Next, the monokaryon culture is prepared at the culture unit utilizing the live culture sample of fungus as shown at block 132. Then, the plurality of fruit bodies is grown in sterile conditions to create the spore stock at the spore stock unit as shown in block 134. Thereafter, the peroxide-based spore rescue and plating process are performed at the plating unit as indicated at block 136. Upon successful germination of the peroxide-based spore, the robust hyphae are sectioned at the section unit as shown in block 138. Next, the robust hyphae are sub-plated and expanded onto a spawn grain master at the sub-plating unit as indicated at block 140. Then, the spawn grain master is subsequently expanded into the appropriate production of spawn volume at the expanding unit as shown in block 142. Finally, the subsequent colonization of a mycelium substrate is performed thereby creating the sheet of mycelium at the colonization unit as shown in block 144.

The foregoing description of the preferred embodiment of the present invention has been presented for the purpose of illustration and description. It is not intended to be exhaustive or to limit the invention to the precise form disclosed. Many modifications and variations are possible in light of the above teachings. It is intended that the scope of the present invention to not be limited by this detailed description, but by the claims and the equivalents to the claims appended hereto.

What is claimed is:

1. A monokaryotic mycelium mass producing system comprising:
   a growing space comprising a tray having a conveying platform and a permeable membrane;
   a substrate inoculated with a fungal strain positioned on the permeable membrane;
   a porous material positioned on top of the substrate;
   a mass of mycelium grown within said growing space and from said mycelium substrate, the mass having a surface of which less than 10% of said surface exhibits the formation of fruiting bodies.

2. The monokaryotic mycelium mass producing system of claim 1 wherein the environment of the growing space is such that the substrate weight to tray empty space volume ratio is between 0.5 and 5.0 g/cc, the tray empty space volume to substrate volume is between 0.01 and 1.0, the tray empty space volume to substrate area is between 0.5 and 5.0 cc/cm$^2$, wherein the $CO_2$ concentration is held above 3% in steady state conditions, the relative humidity is held above 40% in steady state conditions, and wherein the $O_2$ concentration is held below 20% in steady state conditions to promote mycelium growth without the fruiting body.

3. The monokaryotic mycelium mass producing system of claim 1 wherein less than 5% of said surface exhibits the formation of fruiting bodies.

4. The monokaryotic mycelium mass producing system of claim 3 wherein the environment of the growing space is such that the substrate weight to tray empty space volume ratio is between 0.5 and 5.0 g/cc, the tray empty space volume to substrate volume is between 0.01 and 1.0, the tray empty space volume to substrate area is between 0.5 and 5.0 cc/cm$^2$, wherein the $CO_2$ concentration is held above 3% in steady state conditions, the relative humidity is held above 40% in steady state conditions, and wherein the $O_2$ concentration is held below 20% in steady state conditions to promote mycelium growth without the fruiting body.

5. The monokaryotic mycelium mass producing system of claim 1 wherein less than 1% of said surface exhibits the formation of fruiting bodies.

6. The monokaryotic mycelium mass producing system of claim 5 wherein the environment of the growing space is the substrate weight to tray empty space volume ratio is between 0.5 and 5.0 g/cc, the tray empty space volume to substrate volume is between 0.01 and 1.0, the tray empty space volume to substrate area is between 0.5 and 5.0 cc/cm$^2$, wherein the $CO_2$ concentration is held above 3% in steady state conditions, the relative humidity is held above 40% in steady state conditions, and wherein the $O_2$ concentration is held below 20% in steady state conditions to promote mycelium growth without the fruiting body.

7. A monokaryotic mycelium mass producing system comprising:
   a culture unit for preparing a monokaryon culture;
   a plating unit for performing a spore rescue and a plating process;
   a section unit for sectioning a plurality of robust hyphae;
   a sub-plating unit for sub-plating and expanding the plurality of robust hyphae;
   an expanding unit for subsequently expanding the hyphae into appropriate production of spawn volume; and
   a colonization unit for creating a mass of mycelium.

8. The monokaryotic mycelium mass producing system of claim 7 wherein the monokaryon culture is adaptable to prepare substantially defect free mass of mycelium having surface area wherein less than 5% of said surface area exhibits the formation of fruiting bodies.

9. The monokaryotic mycelium mass producing system of claim 7 wherein the monokaryon culture is adaptable to prepare substantially defect free mass of mycelium having surface area wherein less than 1% of said surface area exhibits the formation of fruiting bodies.

10. The monokaryotic mycelium mass producing system of claim 7 wherein the culture unit prepares the monokaryon culture utilizing a live culture sample of a fungal material.

11. The monokaryotic mycelium mass producing system of claim 7 wherein the spore stock unit is designed to grow a plurality of fruit bodies in sterile conditions for creating the spore stock.

12. The monokaryotic mycelium mass producing system of claim 7 wherein the spore rescue process performed by the plating unit is.

13. The monokaryotic mycelium mass producing system of claim 12 wherein the plating unit utilizes the plurality of fruiting bodies for performing the spore rescue and the plating process.

14. The monokaryotic mycelium mass producing system of claim 7 wherein the colonization unit is adaptable to perform a subsequent colonization of a mycelium substrate thereby creating the sheet of mycelium.

* * * * *